United States Patent
Ligugnana et al.

(10) Patent No.: US 9,989,445 B2
(45) Date of Patent: Jun. 5, 2018

(54) DEVICE FOR TAKING AIR SAMPLES FOR THE ENVIRONMENTAL MICROBIOLOGICAL CONTROL

(71) Applicant: Orum International S.r.l., Milan (IT)

(72) Inventors: Roberto Ligugnana, Milan (IT); Sandro Ligugnana, Milan (IT)

(73) Assignee: ORUM INTERNATIONAL S.R.L., Milan (IT)

(*) Notice: Subject to any disclaimer, the term of this patent is extended or adjusted under 35 U.S.C. 154(b) by 29 days.

(21) Appl. No.: 15/178,313

(22) Filed: Jun. 9, 2016

(65) Prior Publication Data

US 2016/0363515 A1    Dec. 15, 2016

(30) Foreign Application Priority Data

Jun. 9, 2015   (IT) .................. 10201521922

(51) Int. Cl.
| G01N 7/00 | (2006.01) |
| G01N 19/10 | (2006.01) |
| G01N 1/24 | (2006.01) |
| H02J 7/02 | (2016.01) |
| H02J 7/00 | (2006.01) |
| G01N 1/22 | (2006.01) |
| G01N 1/26 | (2006.01) |
| H04W 4/00 | (2018.01) |
| H04W 84/18 | (2009.01) |
| H04L 29/08 | (2006.01) |

(52) U.S. Cl.
CPC .......... *G01N 1/24* (2013.01); *G01N 1/2273* (2013.01); *G01N 1/26* (2013.01); *H02J 7/0042* (2013.01); *H02J 7/0052* (2013.01); *H02J 7/025* (2013.01); *G01N 2001/2223* (2013.01); *G01N 2001/2276* (2013.01); *G01N 2001/245* (2013.01); *H02J 2007/0062* (2013.01); *H04L 67/12* (2013.01); *H04W 4/008* (2013.01); *H04W 84/18* (2013.01)

(58) Field of Classification Search
CPC .............................. G01N 1/24; G01N 1/2273
USPC ............................... 73/31.02, 863.23, 863.83
See application file for complete search history.

(56) References Cited

U.S. PATENT DOCUMENTS

| 4,080,832 A | 3/1978 | Moody et al. |
| 5,500,369 A | 3/1996 | Kiplinger |
(Continued)

FOREIGN PATENT DOCUMENTS

| WO | 2003/081212 A2 | 10/2003 |
| WO | 2011/103145 A1 | 8/2011 |

OTHER PUBLICATIONS

Author: unknown, Title: V100 Controller and Air Sampler Users Manual, Date: Nov. 2012, Publisher: EMTEK, LLC., pages total: 83.*

(Continued)

*Primary Examiner* — Lisa Caputo
*Assistant Examiner* — Roger Hernandez-Prewitt
(74) *Attorney, Agent, or Firm* — Ice Miller LLP

(57) ABSTRACT

A device comprises a main body equipped with at least one handle, three sampling chambers that are mounted outside the main body and a control unit. The three sampling chambers are independent of each other and protrude radially from a predefined portion of the main body. The control unit is device can effect multiple environment to be controlled programmed so that the samplings from an in one, two or three different positions in the space, remaining stationary.

16 Claims, 6 Drawing Sheets

(56) References Cited

U.S. PATENT DOCUMENTS

| | | | |
|---|---|---|---|
| 6,094,997 A | | 8/2000 | Lemonnier |
| 6,565,638 B1 | | 5/2003 | Sugita et al. |
| 2008/0087108 A1 | * | 4/2008 | Kreikebaum et al. ............. G01N 1/2202 73/863.23 |
| 2008/0229805 A1 | | 9/2008 | Barket et al. |
| 2009/0268201 A1 | | 10/2009 | Call |
| 2016/0002700 A1 | * | 1/2016 | Ketcham et al. .... G01N 1/2205 435/5 |

OTHER PUBLICATIONS

Author: unknown, Title: Surface Air System (SAS) Monitoring Instruments, Date: 2013, Publisher: VWR International PBI, pages total: 16.*

Author: unknown, Title: "SAS Super 100/180", "Duo SAS Super 360", "SAS Isolator"—Instruction Manual, Date: Oct. 2006, Publisher: International PBI S.p. A., pages total: 48.*

Search Report for IT UB2015A00988, Ministero dello Sviluppo Economico, dated Feb. 16, 2016, pages: 2.

* cited by examiner

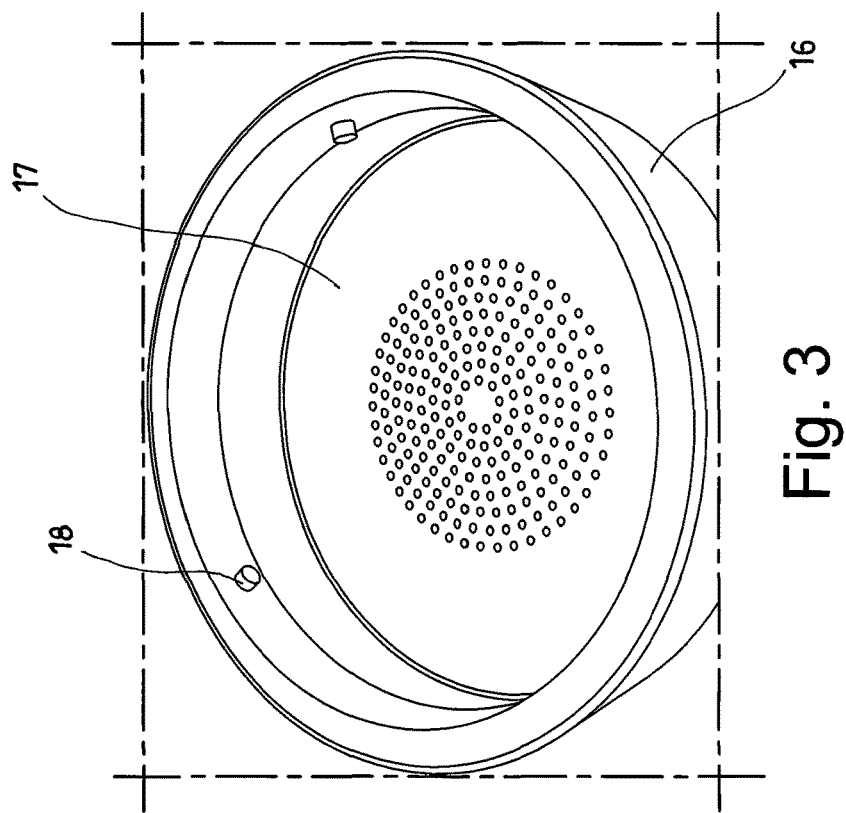
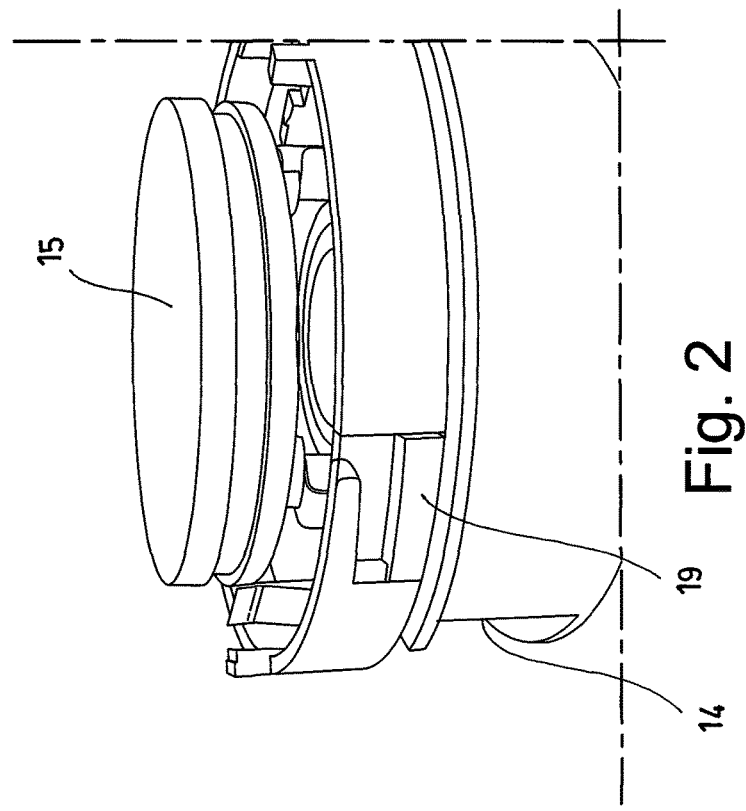

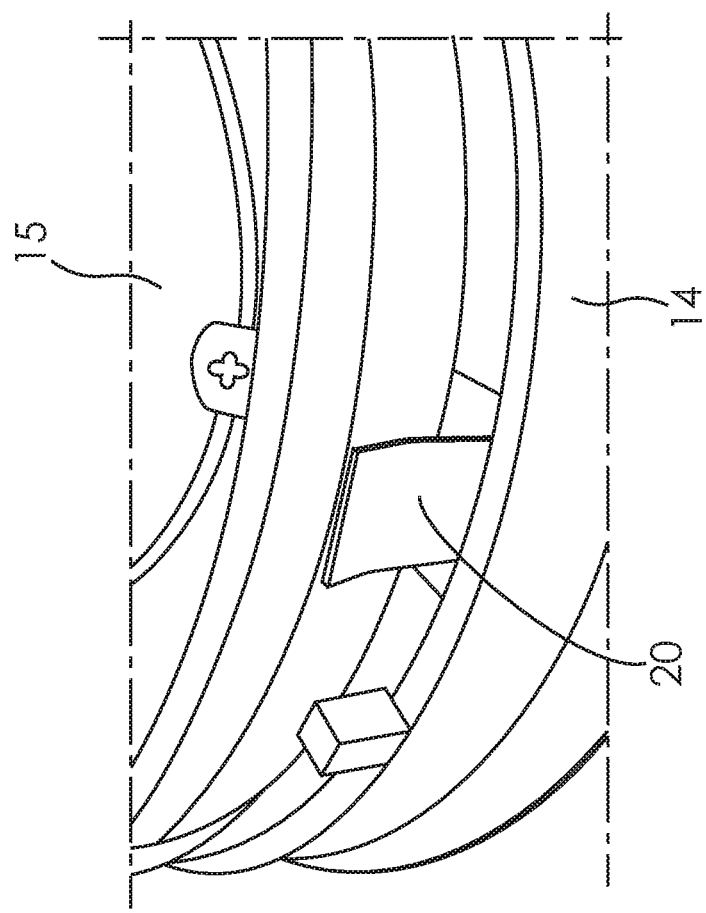
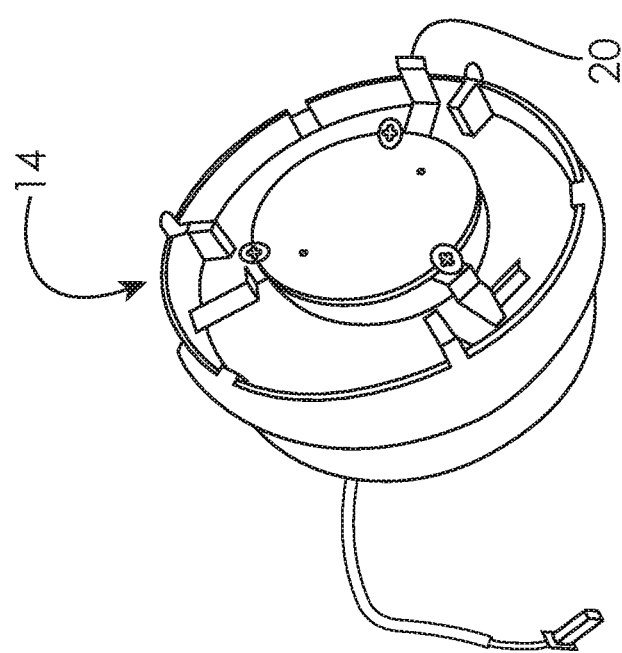
Fig. 4
Fig. 5

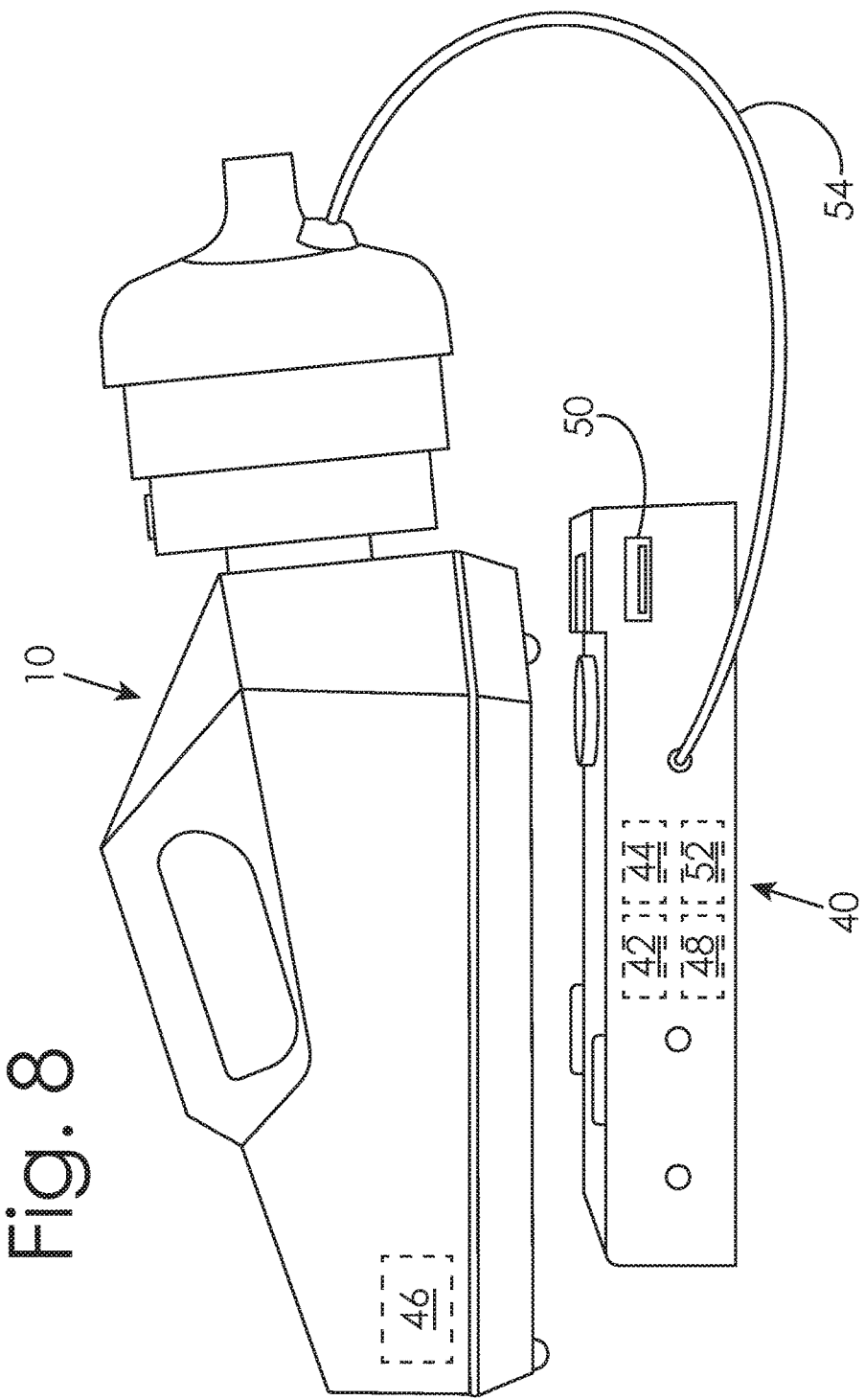

DEVICE FOR TAKING AIR SAMPLES FOR THE ENVIRONMENTAL MICROBIOLOGICAL CONTROL

CROSS-REFERENCE TO RELATED APPLICATIONS

The present application is related to and claims the priority benefit of Italian Patent Application Serial No. 02015000021922, filed Jun. 9, 2015, the text and drawings of which are hereby incorporated by reference in their entireties.

TECHNICAL FIELD

The present invention relates to a device for taking air samples for the environmental microbiological control. In particular, the reference field is represented by those environments that need to be monitored in terms of microbiological control of the air contained therein.

BACKGROUND

The term environment relates both to a closed area, such as a room or a hall, and to open spaces not necessarily enclosed by walls. Among the possible applications, the device could in fact be used:
  in the industry of medical devices production, in which "sterile chambers", where medical devices for human and veterinary use are produced, need to be controlled;
  in the agri-food industry, in which an environmental control must be effected and the processing of food products subject to microbiological degradation is carried out;
  in hospitals, where operating and hospital rooms at high microbiological risk need to be controlled;
  in the electronics industry, in which an environmental control must be effected and microelectronic and aerospace components are produced for the microbiological monitoring of the cabins and shuttles that go into the space.

When the characteristics of a certain environment or sample must be assessed with respect to its content of microorganisms, both devices capable of putting in contact the microorganisms contained in said environmental, and an element for entrapping said microorganisms are used. A type of widely used entrapping element consists of round boxes containing sterile gelatinous mediums, normally based on agar.

Known portable sampling devices currently comprise a main body equipped with a handle that bears, at one of its ends, a support wherein the box containing the gelatinous medium is inserted. The support has an annular structure and the box with the gelatinous medium is placed at a through-hole connected to a suction group. On the box with the gelatinous medium there is a cover equipped with numerous small calibrated holes through which air is sucked.

The traditional devices are also provided with an electronic control unit that controls the switching on and the switching off of the suction unit and implements the timer function. When the device is used for sampling the air contained in a certain environment or volume, the control unit activates the suction group that draws the air, making it pass through the cover with the calibrated holes.

The air comes into contact with the gelatinous medium and deposits onto the same the microorganisms present therein. The gelatinous medium is then analyzed in a known manner and the content of microorganisms in the air is identified.

Portable sampling devices of the known type are described, for example, in documents WO 03/081212 A2, U.S. Pat. No. 5,500,369 A, U.S. Pat. No. 6,565,638 B1 and US 2009/0268201 A1.

The traditional devices of the type indicated above can, in some cases, prove to be not very efficient and may not be indicative of the real content of microorganisms present in the environment or in the area to be analyzed. The air sampling is in fact effected at a narrow range of action and not, as it would be instead desirable, in several positions of the environment to be controlled, subsequently taking an average of the results obtained. In practice, therefore, the sample collected may not be indicative of the actual concentration of microorganisms in the whole environment due to a possible non-uniformity of concentration thereof. Although the problem can be overcome by taking several samplings in the same environment at different times and in different positions, however, also in this manner samples not very significant could be taken since, for example, the microorganisms could move.

Therefore, for sampling a certain environment, device of the known type is currently used so as to effect sequential samplings in different positions. These sequential samplings are effected by fixing the device on a support and programming the control unit so that this activates the suction group at prefixed time intervals. In practice, therefore, the device is switched on and subsequently switched off, controlled by the control unit, at predetermined time intervals between which the device is moved.

Also in this case, however, the samples taken may not be indicative of the actual content of microorganisms since, for example, particular conditions can generate in the environment, such as vortices or pressure and/or temperature gradients, which cause a recirculation of the air around the unique support for the gelatinous medium. Furthermore, since the microorganisms are usually carried by dust particles, even if the device were provided with a particularly efficient suction group, it would never be possible co capture all of the dust and the smallest particles could not be captured by the gelatinous medium. Hence, also in this case, the samples prove to be not particularly indicative of the real content of microorganisms in the environment.

In addition to errors of statistical nature, which per se have a very high incidence in microbiology, the known devices also have the problem that, by increasing the number of "resetting" operations, the device may be more frequently microbiologically contaminated by the manipulation of the operator.

SUMMARY

Starting from this known technique, the objective of the present invention is to make a device for taking air samples for the microbiological control of environments which is alternative to the known devices, particularly efficient and capable of solving the drawbacks indicated above.

According to the most general aspect of the invention, the above objectives are achieved thanks to a device for taking air samples provided with three sampling chambers, so as to be able to take samplings from an environment to be controlled in one, two or three different positions in the space, keeping the device stationary for taking air samples.

Further features of the invention will be highlighted in the subsequent description and dependent claims.

The characteristics and advantages of a device for taking air samples for environmental microbiological control will appear more evident from the following illustrative and non-limiting description, referring to the enclosed schematic drawings.

BRIEF DESCRIPTION OF THE DRAWINGS

FIGS. 2-5 show construction details of the sampling chambers 13, 13', 13" of the device of FIG. 1;

FIG. 8 shows a schematic view of the calibration device associated with the relative base.

DETAILED DESCRIPTION

Figure 1:
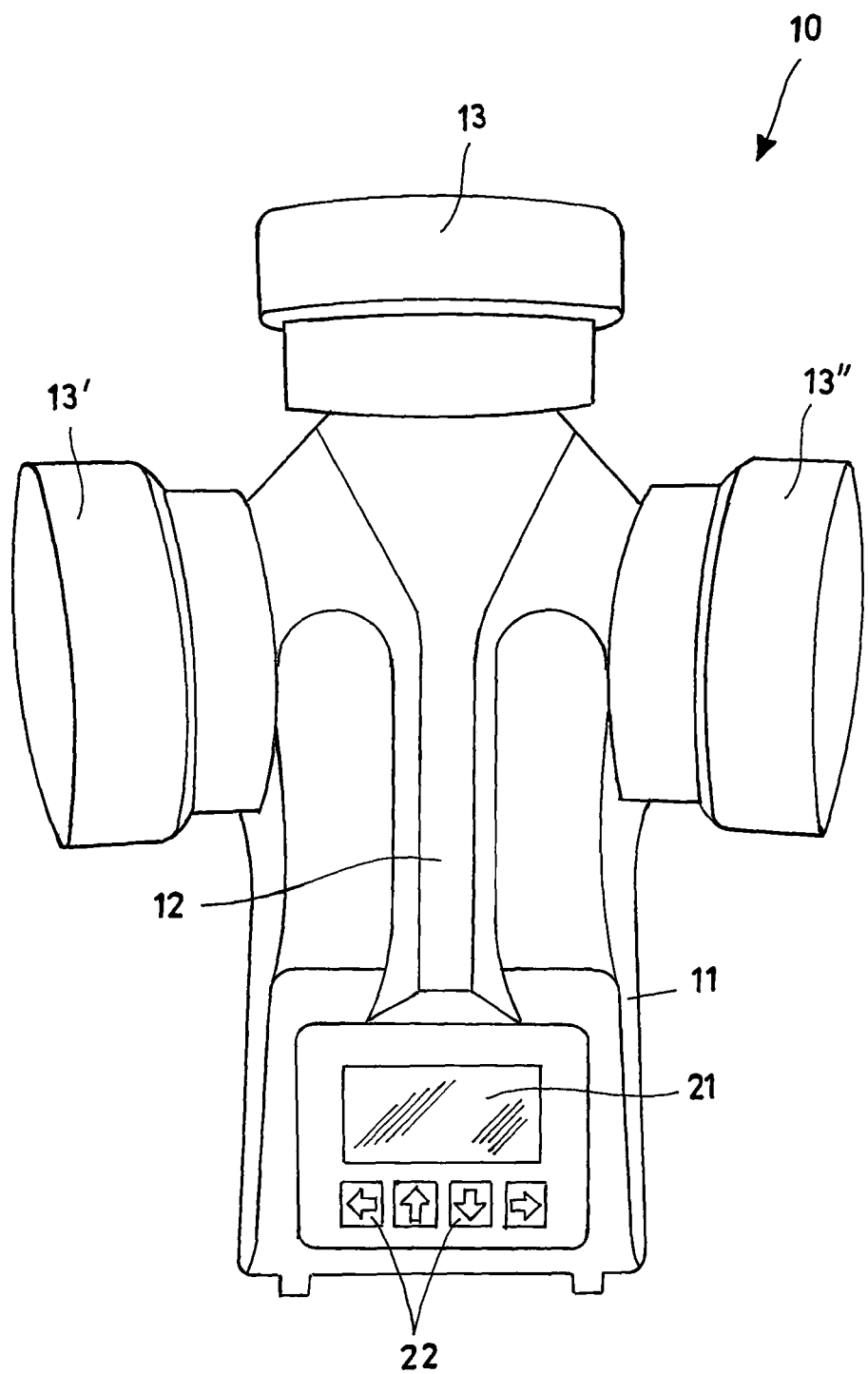
FIG. 1 shows a view of an embodiment of a device for taking air samples for environmental microbiological control according to the present invention.

With reference to the figures, a device for taking air samples for environmental microbiological control according to the present invention is shown with reference number 10. Said device 10 is of the portable type and comprises a main body 11 equipped with at least one handle 12 and with which three sampling chambers 13, 13', 13" separated from each other can be removably coupled.

Figure 7:
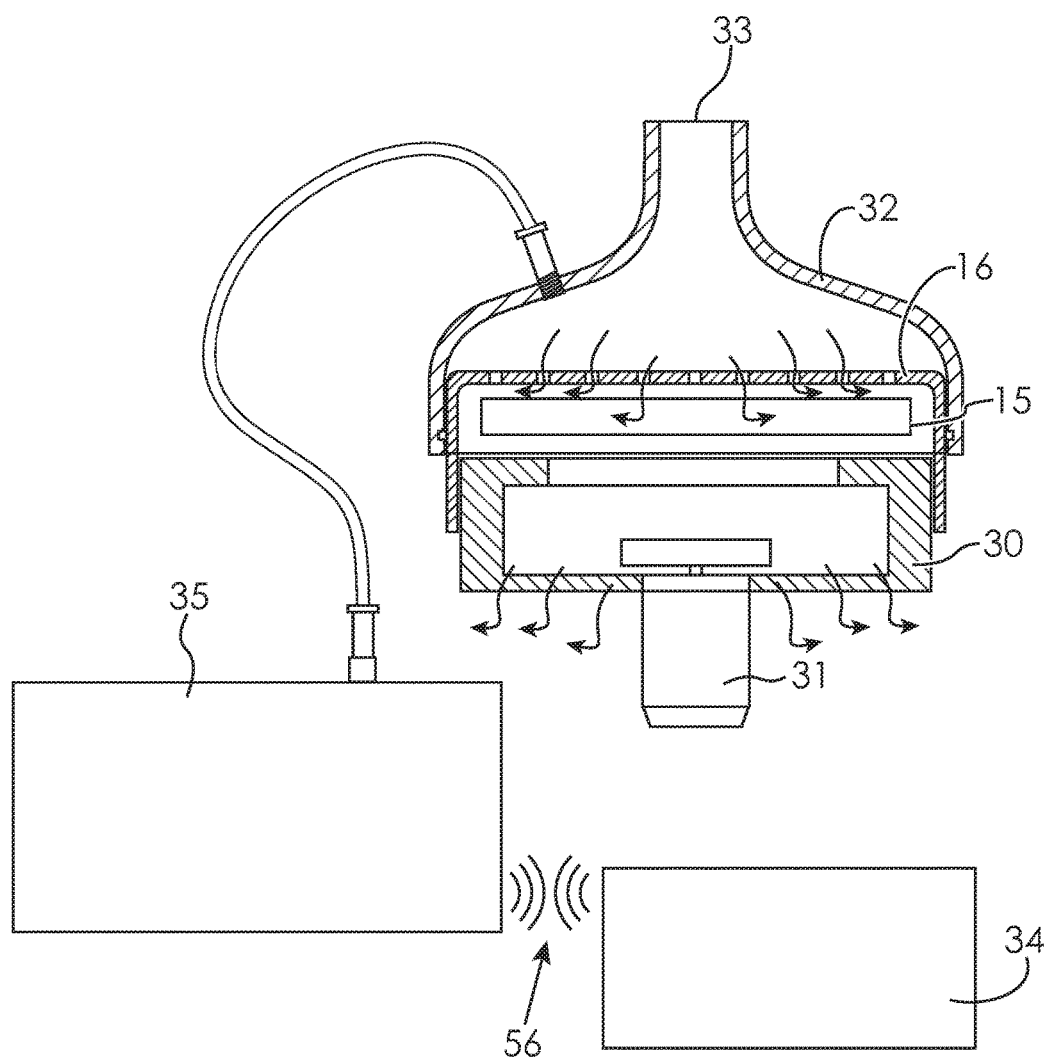
FIG. 7 shows a calibration device that is associable with the sampling chamber 13, 13', 13" of the device of FIG. 1.

As it can be seen in FIG. 1, the device 10 provides the presence of three sampling chambers 13, 13', 13" independent of each other, that protrude radially from a predefined portion of the main body 11 of said device 10. Advantageously, in this case, a control unit 34, schematically shown in FIG. 7, can control the device 10 so that it can take sequential or simultaneous samplings from an environment to be controlled in one, two or three different positions in the space even remaining stationary. The control unit 34 can also comprise pre-set analysis cycles.

Figure 6:
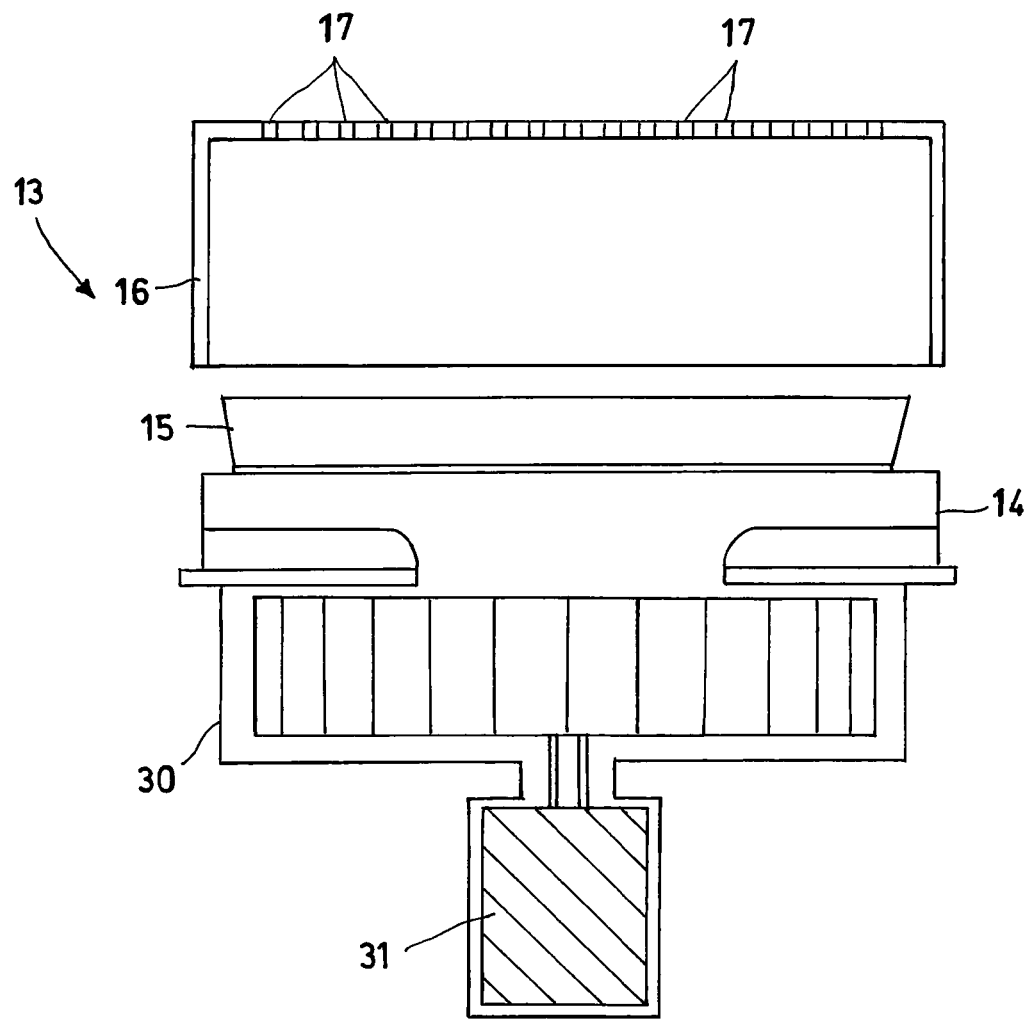
FIG. 6 shows a sectional view of a sampling chamber 13, 13', 13" of the device of FIG. 1.

As it can be seen in FIG. 6, each sampling chamber 13, 13', 13" is independent of the others, as well as removably associable with the device 10. In order to achieve this double objective, each sampling chamber 13, 13', 13" comprises a casing 30, which houses internally a fan motor assembly 31 and, in the internal upper part of which, also a receiving base 14 for receiving a removable sampling support 15.

Since the fan motor assembly 31 is housed and integrated inside the respective sampling chamber 13, 13', 13", advantageously in the case of breakage of the fan motor 31, it is sufficient to substitute the damaged sampling chamber 13, 13', 13" to restore the correct functioning of the device 10. At present, on the contrary, in the presence of similar breakdowns, the whole main body of the device needs to be dismantled to provide for the repair or replacement of the damaged fan motor assembly.

A cover 16 is positioned above the support 15, which is also removable and equipped with a series of small calibrated suction holes 17. The cover 16 is associable with the base 14 by means of a bayonet coupling, FIGS. 2 and 3, which comprises a plurality of pegs 18 on the cover 16 side and a corresponding plurality of slotted seats 19 for receiving and retaining the pegs 18 on the base 14 side. The removable sampling support 15, known per se, is associable with the base 14 by means of elastic metal tabs 20, FIGS. 4 and 5, so that sampling supports 15 having different sizes can be associated with the base 14.

The device 10 comprises a display 21 and a control pushbutton panel 22 configured so as to control the simultaneous or sequential actuation of the sampling chambers 13, 13', 13" and be able to perform all the settings relating to the recording of the detection data. In the embodiment with three sampling chambers 13, 13', 13", the latter are oriented so as to provide a range of action of 210° of the surrounding environment and can be removed with respect to the main body 11.

Advantageously, a calibration device can also be associated with each sampling chamber 13, 13', 13", which, by means of a proportional differential pressure transducer, detects the exact flow-rate of air and enables the operator to periodically control and align, through a simple accessory and without the aid of further instruments, the correct value of the air volumes taken. Said calibration device comprises a cap cover 32 associable around the sampling chamber 13, 13', 13" and provided with a calibrated hole 33.

By activating the suction, the air passing through the calibrated hole 33 creates a depression proportional to the volume sucked. This depression is measured by a transducer 35 and this value allows the volume of sucked air to be accurately identified. By comparing the value measured with that sucked, it is possible to act on the control unit 34 in order to correct any possible errors.

Finally, the device 10 comprises data transmission means of the wireless type for data export, identification of the sampling and induction means for recharging the batteries without the aid of electric connection cables.

Furthermore, as it can be seen in FIG. 8, the device 10 can be associated with a respective support base 40 that incorporates internally some interaction equipment with the device 10 itself. The support base 40 can incorporate, for example:

a sensor 42 for positioning the device 10 on the support base 40, with the actuation of an induction device 44 for recharging the batteries 46;

a system 48 for controlling the current absorption and the automatic switching off upon completion of the battery recharge;

a connection socket 50, for example of the USB type, for recharging remote devices and serial data communication;

the automatic calibration device 52 previously described that sends the data detected to the chamber to be controlled, for example by cable 54 or wireless Bluetooth serial communication 56.

It can thus be seen that the device for taking air samples for environmental microbiological control according to the present invention achieves the objectives previously specified.

The device for taking air samples for environmental microbiological control according to the present invention thus conceived can undergo numerous modifications and variations, all included within the same inventive concept; furthermore, all the details can be substituted by technically equivalent elements. In practice, the materials used, as well as their size, can be of any type according to technical needs.

The invention claimed is:

1. A portable environmental microbiological control device comprising a main body equipped with at least one handle, wherein the device comprises three sampling chambers independent of each other, which protrude radially from a predefined portion of said main body, wherein each sampling chamber comprises a casing for housing a fan motor assembly and, in an upper part of the casing, a receiving base for receiving a removable sampling support and a removable cover that is equipped with a suction grid; the device further comprising a control unit programmed so that the device can effect multiple samplings from an environment to be controlled in one, two or three different positions in space, while remaining stationary.

2. The device according to claim 1, wherein said cover is associable with said base by means of a bayonet coupling that comprises, on the cover side, a plurality of pegs and, on the base side, a corresponding plurality of slotted seats for receiving and retaining said pegs.

3. A sampling assembly comprising a device for taking air samples according to claim 2, and a support base incorporating internally at least one of the following interaction equipment with said device for taking air samples:
   a sensor for positioning said device for taking air samples on said support base, the sensor operative to actuate an induction device for recharging the batteries;
   a system for controlling current absorption and automatic switching off upon completion of a battery recharge;
   a USB connection socket for charging remote devices and for serial data communication;
   an automatic calibration device that sends detected data to the chamber to be controlled by cable or wireless Bluetooth serial communication.

4. The device according to claim 1, wherein said removable sampling support is associable with said base by means of elastic metal tabs so that sampling supports having different sizes can be associated with the base.

5. A sampling assembly comprising a device for taking air samples according to claim 4, and a support base incorporating internally at least one of the following interaction equipment with said device for taking air samples:
   a sensor for positioning said device for taking air samples on said support base, the sensor operative to actuate an induction device for recharging the batteries;
   a system for controlling current absorption and automatic switching off upon completion of a battery recharge;
   a USB connection socket for charging remote devices and for serial data communication;
   an automatic calibration device that sends detected data to the chamber to be controlled by cable or wireless Bluetooth serial communication.

6. The device according to claim 1, comprising a display and a control pushbutton panel configured so as to control simultaneous or sequential actuation of one or more sampling chambers and to control settings relating to recording of detection data.

7. A sampling assembly comprising a device for taking air samples according to claim 6, and a support base incorporating internally at least one of the following interaction equipment with said device for taking air samples:
   a sensor for positioning said device for taking air samples on said support base, the sensor operative to actuate an induction device for recharging the batteries;
   a system for controlling current absorption and automatic switching off upon completion of a battery recharge;
   a USB connection socket for charging remote devices and for serial data communication;
   an automatic calibration device that sends detected data to the chamber to be controlled by cable or wireless Bluetooth serial communication.

8. The device according to claim 1, wherein said sampling chambers are oriented so as to provide a range of action of 210° of a surrounding environment.

9. A sampling assembly comprising a device for taking air samples according to claim 8, and a support base incorporating internally at least one of the following interaction equipment with said device for taking air samples:
   a sensor for positioning said device for taking air samples on said support base, the sensor operative to actuate an induction device for recharging the batteries;
   a system for controlling current absorption and automatic switching off upon completion of a battery recharge;
   a USB connection socket for charging remote devices and for serial data communication;
   an automatic calibration device that sends detected data to the chamber to be controlled by cable or wireless Bluetooth serial communication.

10. The device according to claim 1, wherein said sampling chambers are removably associable with said main body.

11. A sampling assembly comprising a device for taking air samples according to claim 10, and a support base incorporating internally at least one of the following interaction equipment with said device for taking air samples:
   a sensor for positioning said device for taking air samples on said support base, the sensor operative to actuate an induction device for recharging the batteries;
   a system for controlling current absorption and automatic switching off upon completion of a battery recharge;
   a USB connection socket for charging remote devices and for serial data communication;
   an automatic calibration device that sends detected data to the chamber to be controlled by cable or wireless Bluetooth serial communication.

12. The device according to claim 1, comprising wireless data transmission means for data export and identification of a sample without electric connection cables, and further comprising induction means for recharging batteries.

13. A sampling assembly comprising a device for taking air samples according to claim 12, and a support base incorporating internally at least one of the following interaction equipment with said device for taking air samples:
   a sensor for positioning said device for taking air samples on said support base, the sensor operative to actuate an induction device for recharging the batteries;
   a system for controlling current absorption and automatic switching off upon completion of a battery recharge;
   a USB connection socket for charging remote devices and for serial data communication;
   an automatic calibration device that sends detected data to the chamber to be controlled by cable or wireless Bluetooth serial communication.

14. The device according to claim 1, comprising a device for calibrating a bell type suction volume with a calibrated hole that is associable with said sampling chambers, said calibration device comprising a transducer.

15. A sampling assembly comprising a device for taking air samples according to claim 14, and a support base incorporating internally at least one of the following interaction equipment with said device for taking air samples:
   a sensor for positioning said device for taking air samples on said support base, the sensor operative to actuate an induction device for recharging the batteries;
   a system for controlling current absorption and automatic switching off upon completion of a battery recharge;
   a USB connection socket for charging remote devices and for serial data communication;
   an automatic calibration device that sends detected data to the chamber to be controlled by cable or wireless Bluetooth serial communication.

16. A sampling assembly comprising a device for taking air samples according to claim 1, and a support base incorporating internally at least one of the following interaction equipment with said device for taking air samples:
- a sensor for positioning said device for taking air samples on said support base, the sensor operative to actuate an induction device for recharging batteries;
- a system for controlling current absorption and automatic switching off upon completion of a battery recharge;
- a USB connection socket for charging remote devices and for serial data communication;
- an automatic calibration device that sends detected data to the chamber to be controlled by cable or wireless Bluetooth serial communication.

* * * * *